United States Patent [19]
McDonald
[11] 4,168,275
[45] Sep. 18, 1979

[54] PROCESS FOR MODIFYING LINSEED OIL

[75] Inventor: James G. McDonald, 2121-45th Ave., Oakland, Calif. 94601
[73] Assignee: James G. McDonald, Oakland, Calif.

[21] Appl. No.: 838,018
[22] Filed: Sep. 29, 1977
[51] Int. Cl.[2] C07C 53/00; C07C 57/00; C07C 59/00
[52] U.S. Cl. 260/398; 106/288 Q; 106/311; 260/413
[58] Field of Search 260/398, 413 S

[56] References Cited

U.S. PATENT DOCUMENTS

| | | | |
|---|---|---|---|
| 1,987,559 | 1/1935 | Hintermaier | 260/398 |
| 2,125,544 | 8/1938 | Colbeth | 260/398 X |
| 2,187,334 | 1/1940 | Stickdorn | 260/398 |
| 2,209,634 | 7/1940 | Muncie | 260/398 X |
| 2,278,425 | 4/1942 | Colberth | 260/398 |
| 2,298,917 | 10/1942 | Auer | 260/398 X |

*Primary Examiner*—Helen M. S. Sneed
*Attorney, Agent, or Firm*—Townsend and Townsend

[57] ABSTRACT

A process for reacting linseed oil and boric acid by adding to linseed oil heated to at least 260° F., boric acid per se preliminarily dissolved in boiling water, allowing the water-containing mixture to cool and thereafter physically separating the reaction products. When the reaction product is precipitated crystals, such crystals can be further purified by washing with organic solvents.

8 Claims, No Drawings

PROCESS FOR MODIFYING LINSEED OIL

BACKGROUND OF THE INVENTION

This invention relates to the product resulting from the reaction of boric acid with linseed oil in the presence of boiling water. Such reaction products have been found to be particularly useful as an oil-base paint extender.

The use of physical mixtures of organic materials, including linseed oil, has heretofore been proposed as additives to enable water to be incorporated with an oilbase paint; see, for example, U.S. Pat. No. 3,245,821. However, such compositions of matter are merely physical combinations of such materials.

SUMMARY OF THE PRESENT INVENTION

It has now been found that when linseed oil, the oil obtained by expression of flaxseed, is subsequently further heated into a heretofore unknown critical range and successively combined with either boric acid and hot water or a hot aqueous solution containing certain amounts of dissolved boric acid, the resulting reaction product exhibits unique characteristics both as an oil-base paint extender and as a surprisingly effective emollient for treatment of skin burns. In the preferred embodiment, the dissolving of the boric acid in boiling water provides crystals as a major proportion of the reaction product.

Boric acid ($H_3Bo_3$) is known for its usefulness as a mild topical astringent and occurs in the form of colorless, odorless, transparent crystals, white granules or powder. Boric acid is known to have some solubility in both boiling water and glycerol solution of various concentrations.

The phrase "linseed oil" is intended to include those commercially available products that have been subjected to various thermal treatments, such as boiled linseed oil. Alternatively, linseed oil can be obtained by the conventional process of pressing the oil from flaxseed that has been heated to temperatures in the range of 140°-165° F. Conversely, it has been found that flaxseed oil which has been subjected to chemical treatments is not particularly effective in this invention.

Thus, the process of this invention involves heating non-chemically treated linseed oil in an open vessel to a temperature preferably in the range of about 280° F. Slightly lower temperatures, such as 260° F., as well as slightly higher temperatures of up to 320° F., have also been found to be satisfactory. However, temperatures in excess of 340° F. have been found to be detrimental to the process because of an adverse, non-reversible effect on the linseed oil.

It will be appreciated by those skilled in the art that the reactions of this invention can be carried out in a closed vessel under elevated pressure conditions with the result that lower reaction temperatures may be employed. However, under atmospheric pressure conditions, i.e., conditions which exist when the reaction is carried out in an open vessel, the minimum effective temperature to which the linseed oil must be heated, has been found to be 260° F.

Although the amount of water employed in the reaction, whether added separately or in which boric acid is dissolved, can vary widely, it has been found most advantageous to employ a quantity of water corresponding to the quantity of linseed oil with which it is to be combined. Furthermore, while the amount of boric acid that can be employed is only limited by the solubility thereof in boiling water, i.e, 1 gram of boric acid being soluble in 4 ml. of boiling water, concentrations of boric acid exceeding 4 ounces per quart of water have not been found to produce significant increases in the amount of crystals formed. The optimum ratio of linseed oil to water to boric acid, on a weight basis, has been found to be in the range of 12:12:1 to 6:6:1, with a ratio of about 8:8:1 respectively, being preferred.

In the preferred embodiment where the boric acid is preliminarily dissolved in boiling water, cooling the combined liquids to room temperature, causes a substantial portion of the resulting crystals to settle out for ready physical separation by conventional techniques known to those skilled in this art. By concentrating the solution through removal of further quantities of water such as by subsequent heating or vacuum treatment, additional crystal precipitation from the combined solutions is attained.

When the composition of this invention is used as a paint extender, the procedure employed is as follows:

When as little as 1 ounce of the reaction product of this invention is added to a gallon of oil-base paint, the paint is found to be compatible with an additional 1 gallon of water. All that is necessary is to combine the ingredients in a container and mix until the consistency is smooth. The reaction product is found to dissolve in the mixture of what would otherwise be an incompatible combination of water and oil-base paint, with the result that the materials stay uniformly dispersed and are readily applied as a smooth paint, either by brush or spray, which has been found to give exceptional coverage, while retaining brilliance of color even under adverse weather conditions. The term "oil-base" paint is intended to include all interior or exterior, white or colored, gloss, semi-gloss, or flat paint compositions.

In order to demonstrate the subject invention, the following examples are offered by way of illustration and not by way of limitation.

EXAMPLE I

To 1 quart of linseed oil heated to about 280° F. was added a quart of boiling water into which 4 ounces of boric acid had been dissolved. The combined liquids frothed for a substantial period of time, after which it was noted the resulting cooled material displayed 4 distinct layers, an upper layer consisting of non-reacted linseed oil, a second layer composed of a mixture of linseed oil and water, a third layer of water, and a bottom layer of crystals. By first removing the lower layer of crystals and subjecting the remaining layers to temperatures sufficient to evaporate a portion of the water, it was found that substantial additional crystals could be recovered from the water and oil/water layers. The crystals were washed with naphtha. All of the crystals that were recovered exhibited consistent properties with respect to enabling water to be combined with an equal volume of oil-base paint.

EXAMPLE II

To 2 quarts of liquid oil heated to about 340° F. was added 4 ounces boric acid. The combination frothed for a substantial period of time during which the temperature rose to 400° F. The mixture was allowed to stand until the mixture cooled to a temperature below 320° F, whereupon a pint of water was added. The addition of the water caused additional frothing which subsided as the mixture cooled. Upon standing for about a week, it was noted that the resulting cooled material displayed three distinct layers, an upper layer consisting of non-reacted liquid oil, and a lower layer of water, with a second product layer sandwiched therebetween. The product layer was found to be present in an amount corresponding to approximately 80 ounces of liquid, 1 ounce of which was found to be sufficient to enable a gallon of water to be mixed with a gallon of oil-base paint.

EXAMPLE III

One quart of water was brought to a boil in a pressure cooker and 6 tablespoons of boric acid dissolved therein. After allowing the water to cool below its boiling point, one quart of boiled linseed oil was added and the pressure cooker covered, sealed and heated to 165° F. for about 1 hour. The mixture was allowed to cool and an additional quart of water was added, with the result that a layer of crystals settled out below an upper layer of oil and water. A small quantity of the crystals was found to enable water to be combined with an equal volume of oil-base paint.

EXAMPLE IV

To 2 quarts of linseed oil heated to about 280° F. was added a quart of boiling water in which 6 tablespoons of boric acid had been dissolved. The combined liquids frothed for a substantial period of time with the foam attaining a volume of approximately 4 gallons. The mixture was allowed to cool to below 280° F. and an additional quart of water was added. When the composition cooled to room temperature, it consisted of 4 distinct layers, an upper layer of non-reacted linseed oil, a second layer of a mixture of linseed oil and water, a third layer of water, and a bottom layer of crystals. The four layers were present in an approximate volume ratio of 3:1:3:1 for the upper layer, second layer, third layer, and bottom layer, respectively. The crystals were treated as in Example I and found to exhibit similar properties as an oil-base paint extender.

Although the foregoing invention has been described in some detail by way of illustration and example for purposes of clarity and understanding, it will be obvious that certain changes and modifications may be practiced within the scope of the appended claims.

What is claimed is:

1. A process for reacting linseed oil and boric acid, comprising the steps of: heating linseed oil to a temperature in the range of 260°-340° F.; dissolving boric acid in boiling water; maintaining the temperature of said linseed oil while combining therewith said aqueous solution of dissolved boric acid; allowing the combined liquids to cool; and recovering the resulting precipitated crystals from the remaining linseed oil and water, the weight ratio of linseed oil to water to boric acid being in the range of 12:12:1 to 6:6:1.

2. A process in accordance with claim 1 wherein the water is brought to its boiling temperature and said boric acid dissolved therein prior to combining the resulting aqueous solution of dissolved boric acid with said linseed oil.

3. A process in accordance with claim 2 wherein said precipitated crystals are thereafter washed with an organic solvent.

4. A process in accordance with claim 1 wherein the amount of boric acid to linseed oil is in a ratio of about 1:8 by weight.

5. A process in accordance with claim 1 wherein the amount of boric acid to linseed oil is in a ratio of about 4 ounces of boric acid per quart of linseed oil.

6. A process in accordance with claim 4 wherein the heated linseed oil is at a temperature of about 280° F.

7. A process in accordance with claim 3 and further characterized by additional heating of said remaining linseed oil and water at a temperature in the range of 200°-260° F., after initial separation of crystals to evaporate water and precipitate further crystals.

8. The product formed by the process of claim 1.

* * * * *